United States Patent [19]
Caspers

[11] Patent Number: 5,549,709
[45] Date of Patent: Aug. 27, 1996

[54] HYPOBARICALLY-CONTROLLED ARTIFICIAL LIMB FOR AMPUTEES

[76] Inventor: Carl A. Caspers, 510-8 25th Ave. North, St. Cloud, Minn. 56301

[21] Appl. No.: 506,911

[22] Filed: Jul. 26, 1995

[51] Int. Cl.⁶ .................. A61F 2/70; A61F 2/74; A61F 2/80
[52] U.S. Cl. .................. 623/24; 623/26; 623/34; 623/37
[58] Field of Search .................. 623/32–37, 24, 623/26; 601/151, 152

[56] References Cited

U.S. PATENT DOCUMENTS

| | | |
|---|---|---|
| 2,424,278 | 7/1947 | Kunkel . |
| 2,464,443 | 3/1949 | Ganoe et al. ............ 623/26 X |
| 2,606,325 | 8/1952 | Nielson . |
| 2,664,572 | 1/1954 | Blevens . |
| 2,671,225 | 3/1954 | Schoene . |
| 2,696,011 | 12/1954 | Galdik . |
| 3,253,600 | 5/1966 | Scholl . |
| 3,322,873 | 5/1967 | Hitchcock . |
| 3,377,416 | 4/1968 | Kandel . |
| 3,393,407 | 7/1968 | Kandel . |
| 3,557,387 | 1/1971 | Ohlenbusch . |
| 3,631,542 | 1/1972 | Potter . |
| 3,732,578 | 5/1973 | Pollack . |
| 3,751,733 | 8/1973 | Fletcher et al. . |
| 3,858,379 | 1/1975 | Graves et al. . |
| 3,895,405 | 7/1975 | Edwards . |
| 3,975,350 | 8/1976 | Hudgin et al. . |
| 3,991,424 | 11/1976 | Prahl . |
| 4,314,398 | 2/1982 | Petterson . |
| 4,381,768 | 5/1983 | Erichsen et al. . |
| 4,466,936 | 8/1984 | Schapel . |
| 4,479,272 | 10/1984 | Beldzisky . |
| 4,623,354 | 11/1986 | Childress et al. . |
| 4,634,446 | 1/1987 | Kristinsson . |
| 4,635,626 | 1/1987 | Lerman . |
| 4,704,129 | 11/1987 | Massey . |
| 4,822,371 | 4/1989 | Jolly et al. . |
| 4,828,325 | 5/1989 | Brooks . |
| 4,888,829 | 12/1989 | Kleinerman et al. . |
| 4,908,037 | 3/1990 | Ross . |
| 4,922,893 | 5/1990 | Wright et al. .............. 601/152 |
| 4,923,475 | 5/1990 | Gosthnian et al. . |
| 5,007,937 | 4/1991 | Fishman et al. . |
| 5,133,776 | 7/1992 | Crowder . |
| 5,221,222 | 6/1993 | Townes . |
| 5,258,037 | 11/1993 | Caspers . |
| 5,314,497 | 5/1994 | Fay et al. . |

FOREIGN PATENT DOCUMENTS

| | | |
|---|---|---|
| 0261884 | 3/1988 | European Pat. Off. . |
| 0363654 | 4/1990 | European Pat. Off. .............. 623/26 |
| 0650708 | 5/1995 | European Pat. Off. . |

*Primary Examiner*—David H. Willse
*Attorney, Agent, or Firm*—Palmatier, Sjoquist & Helget, P.A.

[57] ABSTRACT

A hypobarically-controlled artificial limb for amputees comprises an outer socket, a flexible, compressible inner socket within the outer socket with a cavity for receiving the residual limb, a space between the inner socket and the outer socket, a vacuum source connected to the cavity, a positive pressure source connected to the space, a regulator for controlling the vacuum source and positive pressure source, and a seal for making an airtight seal between the residual limb and the socket. Another embodiment includes a semi-compressible molding material in the space to mold to the contours of the residual limb under the influence of vacuum and/or positive pressure.

38 Claims, 4 Drawing Sheets

HYPOBARICALLY-CONTROLLED ARTIFICIAL LIMB FOR AMPUTEES

BACKGROUND OF THE INVENTION

The present invention relates to prosthetic devices and more particularly to a hypobarically-controlled artificial limb for amputees.

An amputee is a person who has lost part of an extremity or limb such as a leg or arm which commonly may be termed as a residual limb. Residual limbs come in various sizes and shapes with respect to the stump. That is, most new amputations are either slightly bulbous or cylindrical in shape while older amputations that may have had a lot of atrophy are generally more conical in shape. Residual limbs may further be characterized by their various individual problems or configurations including the volume and shape of a stump and possible scar, skin graft, bony prominence, uneven limb volume, neuroma, pain, edema or soft tissue configurations.

Figures 1, 2, 9:
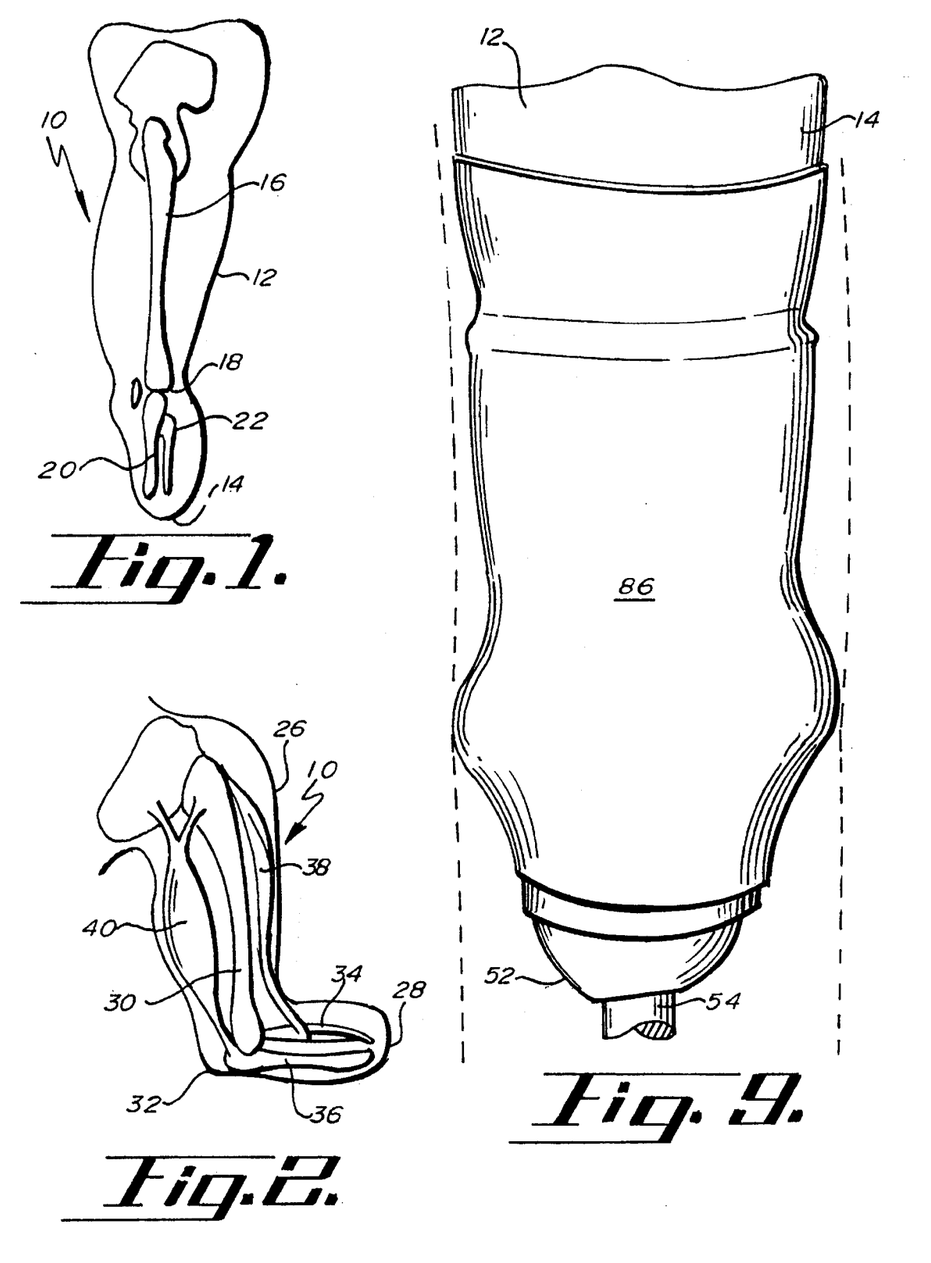
FIG. 1 is a side elevational view of the tissue and skeletal structure of an amputee's residual limb.
FIG. 2 is a side elevational view of a residual limb in the form of an amputated arm showing the skeletal and muscular structure of the residual limb.
FIG. 9 is an elevational view of the polyurethane sleeve and second stretchable nylon sleeve rolled over the socket and residual limb with clothing shown in broken outline.

Referring to FIGS. 1 and 2, a below the knee residual limb 10 is shown and described as a leg 12 having been severed below the knee terminating in a stump 14. In this case, the residual limb 10 includes soft tissue as well as the femur 16, knee joint 18, and severed tibia 20 and fibula 22. Along these bone structures surrounded by soft tissue are nerve bundles and vascular routes which must be protected against external pressure to avoid neuromas, numbness and discomfort as well as other kinds of problems. A below the knee residual limb 10 has its stump 14 generally characterized as being a more bony structure while an above the knee residual limb may be characterized as including more soft tissue as well as the vascular routes and nerve bundles.

Referring to FIG. 2, amputees who have lost a part of their arm 26, which terminates in a stump 28 also may be characterized as having vascular routes, nerve bundles as well as soft and bony tissues. The residual limb 10 includes the humerus bone 30 which extends from below the shoulder to the elbow from which the radius 34 and ulna 36 bones may pivotally extend to the point of severance. Along the humerus bone 30 are the biceps muscle 38 and the triceps muscle 40 which still yet may be connected to the radius 34 and the ulna 36, respectively.

In some respects, the residual limb amputee that has a severed arm 26 does not have the pressure bearing considerations for an artificial limb but rather is concerned with having an artificial limb that is articulable to offer functions typical of a full arm, such as bending at the elbow and grasping capabilities. An individual who has a paralyzed limb would also have similar considerations wherein he or she would desire the paralyzed limb to have some degree of mobility and thus functionality.

Historically, artificial limbs typically used by a leg amputee were for the most part all made out of wood such as an Upland Willow. The limbs were hand carved with sockets for receiving the stump 14 of the residual limb 10. Below the socket would be the shin portion with the foot below the shin. These wooden artificial limbs were covered with rawhide which often were painted. The sockets of most wood limbs were hollow as the limbs were typically supported in the artificial limb by the circumferential tissue adjacent the stump 14 rather than at the distal end of the stump 14.

Some artificial limbs in Europe were also made from forged pieces of metal that were hollow. Fiber artificial limbs were also used which were stretched around a mold after which they were permitted to dry and cure. Again, these artificial limbs were hollow and pretty much supported the residual limb about the circumferential tissue adjacent the stump 14.

All of these various artificial limbs have sockets to put the amputee's stump 14 thereinto. There are generally two categories of sockets. There are hard sockets wherein the stump goes right into the socket actually touching the socket wall without any type of liner or stump sock. Another category of sockets is a socket that utilizes a liner or insert. Both categories of sockets typically were opened ended sockets where they had a hollow chamber in the bottom and no portion of the socket touched the distal end of the stump 14. So, the stump was supported about its circumferential sides as it fits against the inside wall of the sockets.

These types of sockets caused a lot of shear force on the stump 14 as well as had pressure or restriction problems on the nerve bundles and vascular flow of fluid by way of the circumferential pressure effect of the socket on the limb. This pressure effect could cause a swelling into the ends of the socket where an amputee may develop severe edema and draining nodules at the end of their stump 14.

With time, prosthetists learned that by filling in the socket's hollow chamber and encouraging a more total contact with the stump and the socket, the swelling and edema problems could be eliminated. However, the problematic tissue configurations, such as bony prominences, required special consideration such as the addition of soft or pliable materials to be put into the socket.

Today, most artificial limbs are constructed from thermoset plastics such as polyester resins, acrylic resins, polypropylenes and polyethylenes, which are perhaps laminated over a nylon stockinette which also may be impregnated by the various resins.

In the past, most artificial limbs were suspended from the amputee's body by some form of pulley, belt or strap suspension often used with various harnesses and perhaps leather lacers or lacings. Another method of suspending artificial limbs is known as the wedge suspension wherein an actual wedge is built into the socket which is more closed at its top opening. The wedge in the socket cups the medial femoral condyle or knuckle at the abductor tubical. Yet another form of suspension is referred to as the shuttle system or a mechanical hookup or linkup wherein a thin suction liner is donned over the stump that has a docking device on the distal end which mechanically links up with its cooperative part in the bottom of the socket chamber. Sleeve suspensions were also used wherein the amputee may use a latex rubber tube which forms into a rubber-like sleeve which would be rolled on over both the top of the artificial limb and onto the amputee's thigh. The sleeve suspensions have been used in combination with other forms of suspensions techniques.

Both the use of a positive pressure system and the use of a negative pressure system (or hypobaric closed chamber) have been utilized in the field of prosthetics. At one time, for pressure systems "inflatable innertubes" were used to fit into sockets. Presently, there are pneumatic "bags" which are strategically placed over what people consider to be good weight-bearing areas to increase pressure to help accommodate for volume changes within the socket.

The problem with this is that it is a very specific pressure and creates atrophy and loss of tissue dramatically over these high pressure areas. None of these systems employs positive pressure distributed over the total contact area between the residual limb and the artificial limb socket to accommodate volume changes within the socket.

The negative pressure aspects have been utilized for a closed chamber in that a socket is donned by pulling in with a sock, pulling the sock out of the socket and then closing the opening with a valve. This creates a seal at the bottom and the stump is held into the socket by the hypobaric seal. However, there are no systems that employ a negative pressure produced by a vacuum pump to lock the residual limb to the artificial limb.

The older systems were initially started in Germany. They were an open-ended socket, meaning there was an air chamber in the bottom of the socket. This did not work particularly well because it would cause swelling of the residual limb into the chamber created by the negative draw of suspending the weight of the leg and being under a confined area. This would lead to significant edema which would be severe enough to cause stump breakdown and drainage.

It was later discovered in America that total contact was essential between the residual limb and the socket and once you had total contact the weight was distributed evenly or the suspension was distributed over the whole surface of the limb rather than just over the open chamber portion of the socket.

The human body as a whole is under approximately one atmosphere of pressure at sea level. It keeps and maintains a normal fluid system throughout the body. When an amputee dons a prosthesis and begins taking the pressures of transmitting the weight of the body through the surface area of the residual limb to the bone, there is increased pressure on the residual limb equal to one atmosphere plus whatever additional pressures are created by weight bearing. This increased pressure causes the eventual loss of fluids within the residual limb to the larger portion of the body which is under less pressure. This loss of fluids causes the volume of the residual limb to decrease during the day. It varies from amputee to amputee, but it is a constant among all amputees and the more "fleshy" and the softer the residual limb, the more volume fluctuation there will be. The greater the weight and the smaller the surface area, the greater the pressures will be and the more "swings" there will be in fluids. In the past, the amputee had to compensate for this volume decrease by removing the artificial limb and donning additional stump socks to make up for the decreased residual limb volume.

While some of these devices addressed some of the problems associated with prosthetics, none of the artificial limbs, liners and sockets, individually or in combination, offered a prosthesis that presented a total contact relationship with the residual limb; absorbed and dissipated shear, shock and mechanical forces transmitted to the limb tissues by the artificial limb; controlled residual limb volume; used negative pressure as a locking device to hold the residual limb into the socket; and used positive pressure not for specific weight bearing, but to totally adjust and adapt the internal socket environment.

There is a need for an improved hypobarically-controlled artificial limb that will offer total contact relationship with the residual limb; absorb and dissipate shock, mechanical and shear forces typically associated with ambulation, twisting and turning and weight bearing with an artificial limb; control residual limb volume by way of even weight distribution; use negative pressure as a locking device to hold the residual limb into the socket; use positive pressure to totally adjust and adapt the internal socket environment to changes in residual limb volume; and control stump volume changes by cooperation between a negative pressure system and a positive pressure system.

In the past, artificial limbs had to be custom-built for the amputee. The custom building process generally consisted of: placing a singly ply thin cotton casting sock over the residual limb; making a first negative mold of the residual limb by forming an orthopedic plaster wrap about the residual limb and casting sock; making a first positive model of the residual limb by filling the negative mold with plaster; forming a thermoplastic foam about the positive model to create a space for a liner; adding additional thermoplastic foam to form a distal end cap as well as other areas which may require additional thicknesses due to tissue configurations; forming a second enlarged negative plaster mold about the foam; removing the foam; pouring a liquid and moldable liner into the space between the positive model and the second negative mold; allowing the liner to harden; removing the liner from the second negative mold; having the amputee don the liner over the residual limb; placing another single ply thin casting sock over the liner; making a third plaster wrap or negative mold of the artificial limb socket about the residual limb and the liner; removing the liner from the third plaster wrap; making a plaster cast or positive model of the socket from dental plaster; milling or shaving the positive model to create a reduced positive model to create weight bearing areas and compression of the liner against the residual limb and the socket; and making the socket from the reduced positive model.

This custom-building process is expensive, time-consuming, and requires the constant attention of a skilled prosthetist.

For third-world countries, there is a need for a generic artificial limb socket which can be fitted to the contours of the residual limb without the need for a lengthy, expensive custom-molding process. The socket should contain a semi-compressible molding material which can be molded to the contours of the residual limb under vacuum and/or positive air pressure.

SUMMARY OF THE INVENTION

A hypobarically-controlled artificial limb for amputees comprises an outer socket, a flexible, compressible inner socket within the outer socket with a cavity for receiving the residual limb, a space between the inner socket and the outer socket, a vacuum source connected to the cavity, a positive pressure source connected to the space, a regulator for controlling the vacuum source and positive pressure source, and a seal means for making an airtight seal between the residual limb and the socket. Another embodiment includes a semi-compressible molding material in the space to mold to the contours of the residual limb under the influence of vacuum and/or positive pressure.

A principle object and advantage of the present invention is that it uses vacuum within the artificial limb socket to suspend the artificial limb from the residual limb.

Another object and advantage of the present invention is that it uses vacuum within the artificial limb socket to compensate for socket fit and volumetric changes within the socket.

Another object and advantage of the present invention is that it uses vacuum within the socket to lock the residual limb into the socket while preventing negative draw within the socket from causing swelling of the residual limb into the socket.

Another object and advantage of the present invention is that it uses vacuum within the socket to oppose the loss of fluids from the residual limb caused by weight-bearing pressures.

Another object and advantage of the present invention is that it uses positive pressure within the socket to automatically reduce socket volume to compensate for fluid loss in the residual limb.

Another object and advantage of the present invention is that it uses both vacuum and positive pressure working together to lock the residual limb into the socket and reduce socket volume to compensate for fluid loss in the residual limb.

Another object and advantage of the present invention is that both the vacuum and the positive pressure may be created by a miniaturized pump with a motor drive.

Another object and advantage of the present invention is that it includes a digital computer system to control the miniaturized pump to regulate both negative pressure and positive pressure.

Another object and advantage of the present invention is that it includes a semi-compressible molding material between the outer socket and the inner socket which may be molded to the contours of the artificial limb under the influence or vacuum and/or positive pressure, thereby avoiding the need for a custom-building process.

DESCRIPTION OF THE PREFERRED EMBODIMENT

Figure 3:
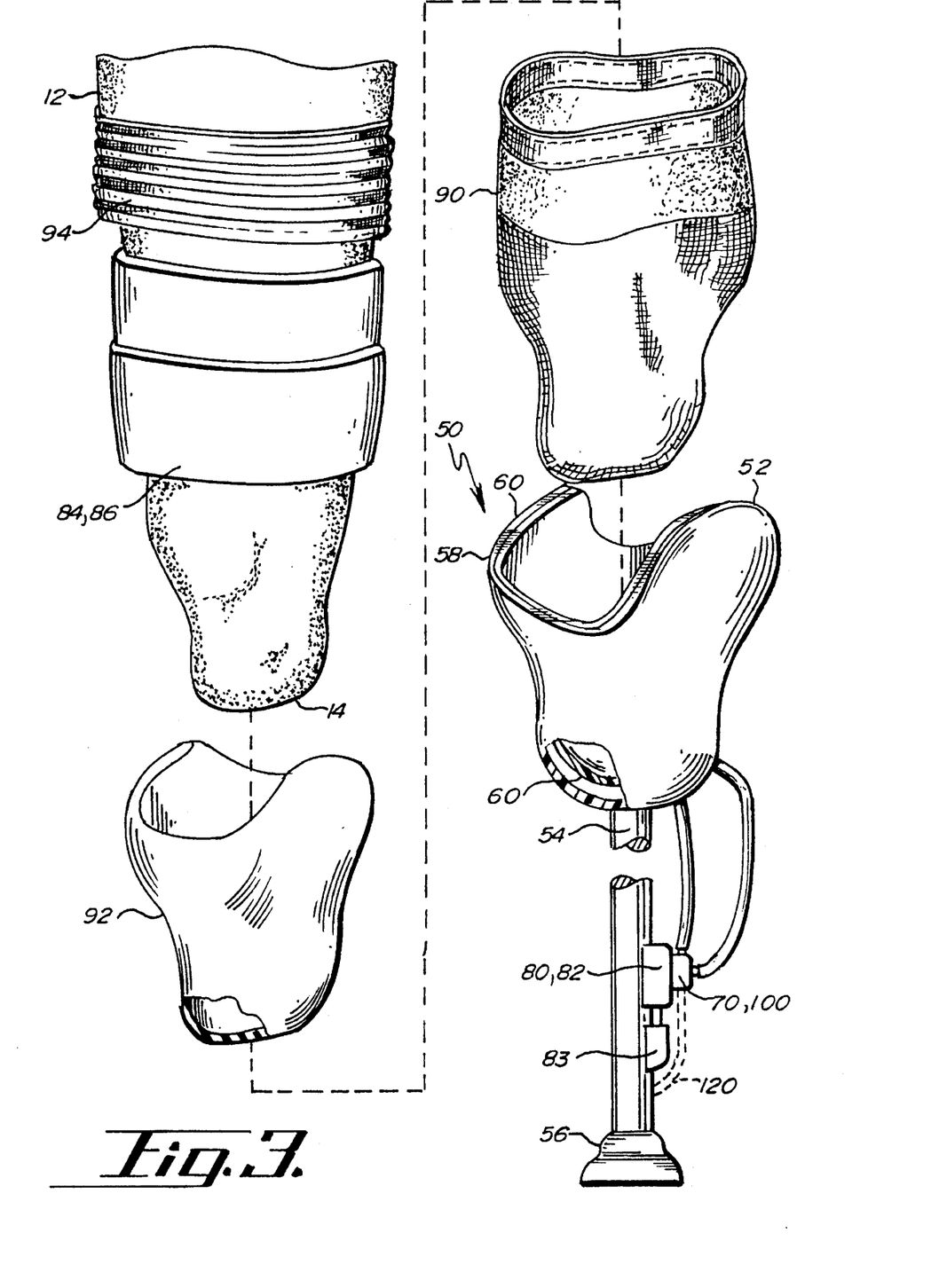
FIG. 3 is an exploded elevational view of the residual limb donning the polyurethane sleeve, stretchable nylon sleeve, liner, nylon sheath and socket of an artificial limb.

FIG. 3 shows the hypobarically-controlled artificial limb 50 of the present invention. The hypobarically-controlled artificial limb 50 includes an outer socket 52, shin 54, and foot 56. The outer socket 52 has a volume and shape to receive a substantial portion of the residual limb 14 with a space 58 therebetween.

Figures 4, 5, 6:
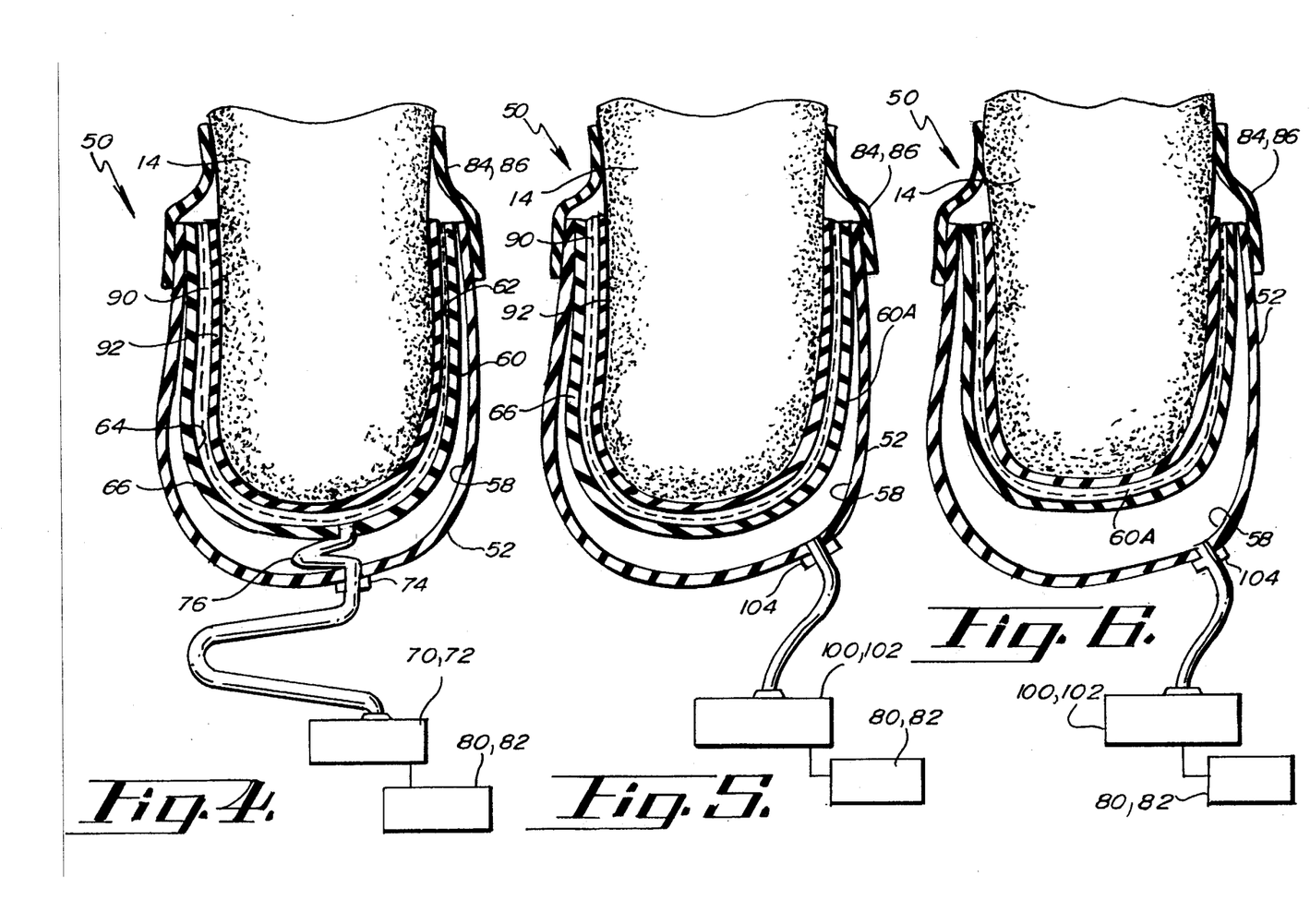
FIG. 4 is a cross-section of the artificial limb and the residual limb along the lines A—A in FIG. 4, showing a first embodiment of the artificial limb.
FIG. 5 is a cross-section of the artificial limb and the residual limb along the lines A—A in FIG. 4, showing a second embodiment of the artificial limb.
FIG. 6 is the same as FIG. 6, but showing compression of the inner socket under the influence of positive air pressure.

A first embodiment of the hypobarically-controlled artificial limb 50 is shown in FIG. 4. The hypobarically-controlled artificial limb 50 further includes a flexible inner socket 60 with a cavity 62 with a volume and shape for receiving a substantial portion of the residual limb 14 and fitting in the space 58 between the outer socket 52 and the residual limb 14. The inner socket 60 has an inner surface 64 opposing the residual limb 14 and an outer surface 66 opposing the outer socket 52.

A vacuum source 70 may conveniently be attached to the shin 54. The vacuum source 70 may preferably be a motor-driven pump 72. The vacuum source 70 is connected to a power source 83, which may be a battery.

A vacuum valve 74 is suitably connected to the vacuum source 70. The vacuum valve 74 may preferably be disposed on the outer socket 52. A vacuum tube 76 connects the vacuum valve 74 to the cavity 62. It will be seen that the vacuum source will cause the residual limb 14 to be drawn into firm contact with the inner surface 64 of the inner socket 60.

The hypobarically-controlled artificial limb 50 also includes a regulator means 80 for controlling the vacuum source 70. Preferably, the regulator means 80 may be a digital computer 82. Alternately, the regulator means may be a vacuum regulator. The regulator means 80 is connected to a power source 83, which may be a battery.

A seal means 84 makes an airtight seal between the residual limb 14 and the outer socket 52. Preferably, the seal means 84 is a nonfoamed, nonporous polyurethane suspension sleeve 86 which rolls over and covers the outer socket 52 and a portion of the residual limb 14. Alternatively, the seal means 84 may be any type of seal which is airtight.

The hypobarically-controlled artificial limb 50 may also include a thin sheath 90 between the residual limb 14 and the inner surface 64 of the inner socket 60. As vacuum is applied to the cavity 62, the sheath 90 will allow the vacuum to be evenly applied throughout the cavity 62. Without the sheath 90, the residual limb 14 might "tack up" against the inner surface 64 and form a seal which might prevent even application of the vacuum to the cavity 62. The sheath 90 may also be used to assist the amputee into a smooth and easy fitting into the inner socket 60. The sheath 90 is preferably made of thin knitted nylon.

The hypobarically-controlled artificial limb 50 may also include a nonfoamed, nonporous polyurethane liner 92 receiving the residual limb 14 and disposed between the sheath 90 and the residual limb 14. The liner 92 provides a total-contact hypobaric suction, equal weight distribution socket liner. The liner 92 readily tacks up to the skin of the residual limb 14 and provides total contact with the limb 14. The liner 92 absorbs and dissipates shock, mechanical and shear forces typically associated with ambulation.

The hypobarically-controlled artificial limb 50 may also include a stretchable nylon second sleeve 94 for rolling over and covering the suspension sleeve 86 to prevent clothing from sticking to and catching the suspension sleeve 86.

Referring to FIG. 3, the polyurethane tubular sleeve 86 may be appreciated alone and in combination with the urethane liner 92 together with the optional nylon sheath 90 and second stretchable nylon sleeve 94.

More specifically, the amputee takes the stretchable nylon second sleeve 94, suitably made of a spandex-like material and rolls it up over the stump 14 to the upper portions of the residual limb suitably as the thigh of a leg 12. Next, the polyurethane sleeve 86 is also rolled upwardly over the residual limb 10. Thereafter, the liner 92 is optionally donned.

Next, the amputee may optionally utilize the nylon sheath 90 which is suitably of a nonstretching, thin, friction reducing nylon. As stated, this sheath 90 optionally may be used to assist the amputee into a smooth and easy fitting into the inner socket 60. Alternatively, the sheath 90 may be avoided and the liner 92 simply inserted into the inner socket 60 of the artificial limb 50.

Next, the amputee simply grasps the rolled over portion of the polyurethane sleeve 86 and rolls it over a substantial portion of the outer socket 52. The sleeve 86 makes an airtight seal between the residual limb 14 and the outer socket 52.

As can be appreciated, the polyurethane sleeve 86 is tacky. Consequently, the stretchable nylon second sleeve 94 may be utilized and rolled over the polyurethane sleeve 86.

The amputee then sets the regulator means 80 to cause the vacuum source 70 to apply vacuum through the vacuum valve 74 and vacuum tube 76 to the cavity 62. Enough vacuum is applied to cause the residual limb (with optional coverings) to be drawn firmly against the inner surface 64 of the inner socket 60, which is flexible. The vacuum source 70 may preferably maintain a vacuum in the range of 0 to 25 inches of mercury.

It will be seen that the vacuum within the inner socket 60 will cause the hypobarically-controlled artificial limb 50 to be suspended from the residual limb 14. The vacuum will lock the residual limb 14 into the inner socket 60 without causing swelling of the residual limb into the socket, because of the total contact of the residual limb 14 with the inner socket 60. That is, there is no open chamber between the residual limb 14 and the inner socket 60 which would draw on the residual limb.

As the volume of the residual limb 14 decreases during the day due to weight-bearing pressures, the regulator means 70 may appropriately adjust the vacuum source 70 to draw the residual limb 14 more firmly against the inner socket 60 and thus compensate for the loss of residual limb volume. The vacuum may also partially oppose the loss of fluids from the residual limb caused by weight-bearing pressures.

A second embodiment of the hypobarically-controlled artificial limb 50 is shown in FIGS. 5 and 6. The second embodiment of the hypobarically-controlled artificial limb 50 is as described above, with the exception that the inner socket 60A is compressible as well as being flexible. Instead of a vacuum source, the second embodiment has a positive air pressure source 100, which may preferably be a motor-driven pump 102. The regulator means 80, which may be a digital computer 82, controls the positive air pressure source 100. The regulator means and positive air pressure source 100 are connected to a power source 83, which may be a battery. A positive pressure valve 104 connects the space 58 to the positive air pressure source 100, for compressing the inner socket 60A as the volume of the residual limb decreases.

It will be seen that as the volume of the residual limb 14 decreases during the day due to weight-bearing pressures, the regulator means 80 may control the positive air pressure source 100 to cause air pressure to compress the inner socket 60A to compensate for the decreased volume of the residual limb, as shown in FIG. 6.

Figure 7:
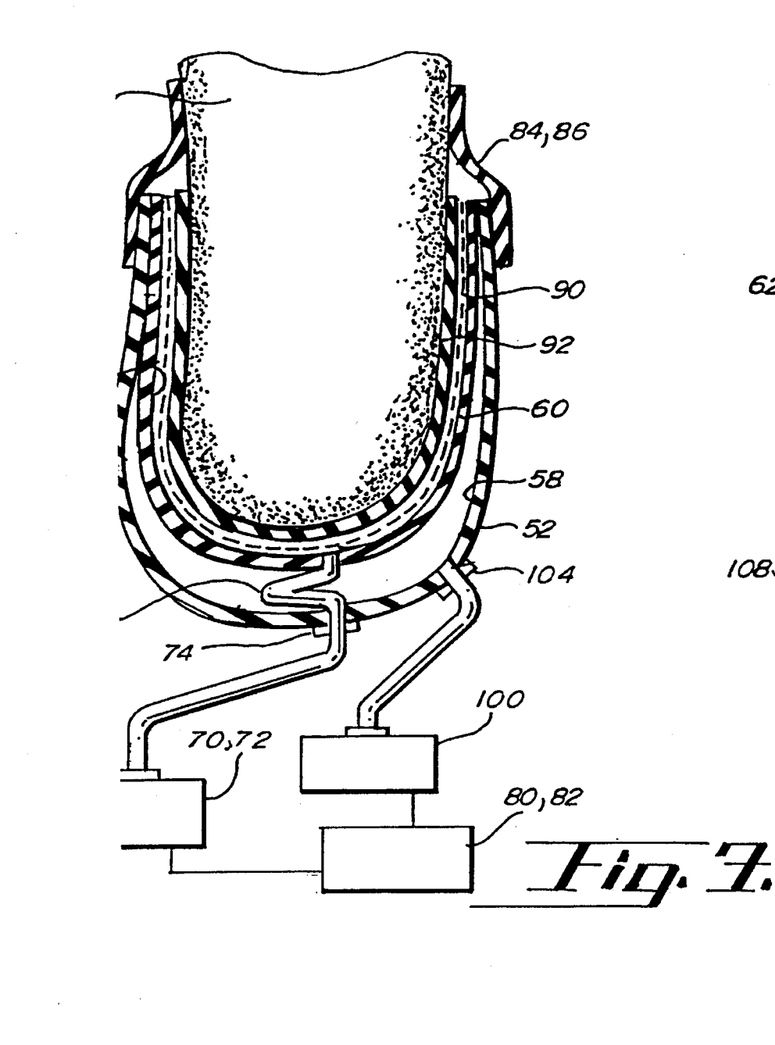
FIG. 7 is a cross-section of the artificial limb and the residual limb along the lines A—A in FIG. 4, showing a third embodiment of the artificial limb.

A third embodiment of the hypobarically-controlled artificial limb 50 is shown in FIG. 7. The third embodiment is a combination of the first and second embodiments described above.

The motor-driven pump 72 may act as both the vacuum source 70 and the positive air pressure source 100. The regulator means 80, vacuum source 70 and positive air pressure source 100 are connected to a power source 83, which may be a battery.

The vacuum source 70, under control of the regulator means 80, will compensate for reduced residual limb volume up to a certain point. From that point on, the regulator means 80 will cause the positive air pressure source 100 to further compensate for reduced residual limb volume as described above. The third embodiment thus uses both vacuum and positive air pressure working together to lock the residual limb 14 into the inner socket 60 and reduce socket volume to compensate for fluid loss in the residual limb 14. The exact point at which the changeover is made between vacuum compensation and positive air pressure compensation is controlled by the regulator means 80, which as described may be a digital computer appropriately programmed for the socket environment.

Figure 8:
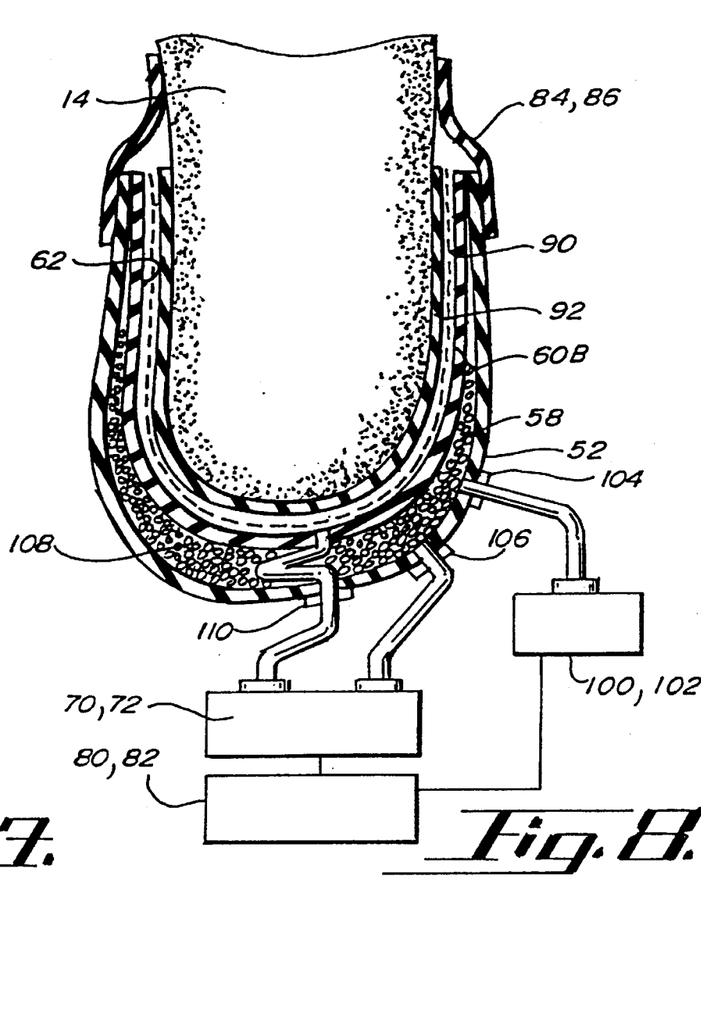
FIG. 8 is a cross-section of the artificial limb and the residual limb along the lines A—A in FIG. 4, showing a fourth embodiment of the artificial limb.

A fourth embodiment of the hypobarically-controlled artificial limb 50 is shown in FIG. 8. The fourth embodiment is like the first embodiment, but includes two vacuum valves: a first vacuum valve 106 and a second vacuum valve 110, both connected to the vacuum source 70. The first vacuum valve 106 connects the vacuum source 70 to the space 58. The space 58 contains a semi-compressible material 108, such as polystyrene beads, as disclosed in U.S. Pat. No. 4,828,325, herein incorporated by reference.

To don the artificial limb 50, the amputee proceeds as described above. After inserting the residual limb 14 (with optional coverings) into the inner socket 60B, which is both compressible and expandable, and rolling the suspension sleeve 86 over the outer socket 52, the amputee activates the regulator means 80, causing the vacuum source 70 to apply a vacuum to the space 58. This causes the material 108 to lock mechanically together into a rigid mass, conforming to the shape of the residual limb 14. The inner socket 60B may expand slightly under the weight of the residual limb 14 and under the influence of vacuum.

It will be seen that the semi-compressible molding material 108 can be molded to the contours of the residual limb 14 without using a custom-building process to produce a custom socket. The outer socket 52 may appropriately occur in standard sizes, such as small, medium, and large. The inner socket 60B may also occur in standard sizes such as small, medium, and large. Adaptation of the inner socket 60B to the contours of the residual limb 14 occurs through solidifying the material 108 under the influence of vacuum.

The second vacuum valve 110 connects the vacuum source 70 to the cavity 62 as previously described, for locking the residual limb 14 into the inner socket 60B.

The fourth embodiment may also include a positive air pressure source 100 as previously described, to adjust the size of the inner socket 60B to compensate for decreased residual limb volume.

The fourth embodiment may also include a thin sheath 90, liner 92, and second sleeve 94, as previously described.

The positive air pressure source 100 may also be used for shock absorption and a dynamic response in the ankle and foot sections of the artificial limb 50, by means of a connection 120.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A hypobarically-controlled artificial limb for amputees who have a residual limb, the artificial limb comprising:

(a) an outer socket with a volume and shape to receive a substantial portion of the residual limb with a space therebetween;

(b) a flexible inner socket with a cavity with a volume and shape for receiving a substantial portion of the residual limb and fitting in said space between said outer socket and the residual limb, said inner socket having an inner surface and an outer surface, said inner surface adapted to oppose the residual limb, said outer surface opposing said outer socket;

(c) a vacuum source;

(d) a vacuum valve connected to said vacuum source and a vacuum tube connecting said vacuum valve to said cavity, thereby drawing the residual limb into firm contact with said inner surface of said inner socket;

(e) a regulator means for controlling said vacuum source;

(f) a power source connected to said regulator means and said vacuum source; and (g) a seal means for making an airtight seal between the residual limb and said outer socket.

2. The hypobarically-controlled artificial limb of claim 1, further comprising a thin sheath to be disposed between the residual limb and said inner surface of said inner socket.

3. The hypobarically-controlled artificial limb of claim 2, further comprising a nonfoamed, nonporous polyurethane liner for receiving the residual limb and to be disposed between said sheath and the residual limb.

4. The hypobarically-controlled artificial limb of claim 2, wherein said sheath is thin knitted nylon.

5. The hypobarically-controlled artificial limb of claim 1, wherein said vacuum source is a motor-driven pump.

6. The hypobarically-controlled artificial limb of claim 1, wherein said regulator means is a digital computer.

7. The hypobarically-controlled artificial limb of claim 1, wherein said seal means comprises a nonfoamed, nonporous polyurethane suspension sleeve for rolling over and covering said outer socket and a portion of the residual limb, thereby forming an airtight seal.

8. The hypobarically-controlled artificial limb of claim 7, further comprising a stretchable nylon second sleeve for rolling over and covering said suspension sleeve to prevent clothing from sticking to and catching said suspension sleeve.

9. A hypobarically-controlled artificial limb for amputees who have a residual limb, the artificial limb comprising:

(a) an outer socket with a volume and shape to receive a substantial portion of the residual limb with a space therebetween;

(b) a flexible, compressible inner socket with a cavity with a volume and shape for receiving a substantial portion of the residual limb and fitting in said space between said outer socket and the residual limb, said inner socket having an inner surface and an outer surface, said inner surface adapted to oppose the residual limb, said outer surface opposing said outer socket;

(c) a positive air pressure source;

(d) a positive pressure valve connecting said space to said positive air pressure source, for compressing said inner socket as the volume of the residual limb decreases;

(e) a regulator means for controlling said positive pressure source;

(f) a power source connected to said regulator means and said positive air pressure source; and (g) a seal means for making an airtight seal between the residual limb and said socket.

10. The hypobarically-controlled artificial limb of claim 9, wherein said positive pressure source is a motor-driven pump.

11. The hypobarically-controlled artificial limb of claim 9, wherein said regulator means is a digital computer.

12. The hypobarically-controlled artificial limb of claim 9, wherein said seal means comprises a nonfoamed, nonporous polyurethane suspension sleeve for rolling over and covering said socket and a portion of the residual limb, thereby forming an airtight seal.

13. The hypobarically-controlled artificial limb of claim 12, further comprising a stretchable nylon second sleeve for rolling over and covering said suspension sleeve to prevent clothing from sticking to and catching said suspension sleeve.

14. The hypobarically-controlled artificial limb of claim 9, further comprising a thin sheath to be disposed between the residual limb and said inner surface of said inner socket.

15. The hypobarically-controlled artificial limb of claim 14, further comprising a nonfoamed, nonporous polyurethane liner for receiving the residual limb and to be disposed between said sheath and the residual limb.

16. A hypobarically-controlled artificial limb for amputees who have a residual limb, the artificial limb comprising:

(a) an outer socket with a volume and shape to receive a substantial portion of the residual limb with a space therebetween;

(b) a flexible, compressible inner socket with a cavity with a volume and shape for receiving a substantial portion of the residual limb and fitting in said space between said outer socket and the residual limb, said inner socket having an inner surface and an outer surface, said inner surface adapted to oppose the residual limb, said outer surface opposing said outer socket;

(c) a vacuum source;

(d) a positive air pressure source;

(e) a vacuum valve connected to said vacuum source and a vacuum tube connecting said vacuum valve to said cavity, thereby drawing the residual limb into firm contact with said inner surface of said inner socket;

(f) a positive pressure valve connecting said space to said positive air pressure source, for compressing said inner socket as the volume of the residual limb decreases;

(g) a regulator means for controlling said vacuum source and said positive pressure source;

(h) a power source connected to said regulator means, said vacuum source, and said positive air pressure source; and (i) a seal means for making an airtight seal between the residual limb and said outer socket.

17. The hypobarically-controlled artificial limb of claim 16, further comprising a thin sheath to be disposed between the residual limb and said inner surface of said inner socket, for producing a uniform region of negative pressure within said cavity in response to said vacuum source.

18. The hypobarically-controlled artificial limb of claim 17, wherein said sheath is thin knitted nylon.

19. The hypobarically-controlled artificial limb of claim 16, wherein said vacuum source is a motor-driven pump.

20. The hypobarically-controlled artificial limb of claim 16, wherein said positive pressure source is a motor-driven pump.

21. The hypobarically-controlled artificial limb of claim 16, wherein a motor-driven pump comprises both said vacuum source and said positive pressure source.

22. The hypobarically-controlled artificial limb of claim 16, wherein said regulator means is a digital computer.

23. The hypobarically-controlled artificial limb of claim 16, wherein said seal means comprises a nonfoamed, nonporous polyurethane suspension sleeve for rolling over and covering said socket and a portion of the residual limb, thereby forming an airtight seal.

24. The hypobarically-controlled artificial limb of claim 23, further comprising a stretchable nylon second sleeve for rolling over and covering said suspension sleeve to prevent clothing from sticking to and catching said suspension sleeve.

25. The hypobarically-controlled artificial limb of claim 17, further comprising a nonfoamed, nonporous polyurethane liner for receiving the residual limb and to be disposed between said sheath and the residual limb.

26. A hypobarically-controlled artificial limb for amputees who have a residual limb, the artificial limb comprising:
  (a) an outer socket with a volume and shape to receive a substantial portion of the residual limb with a space therebetween;
  (b) a flexible, compressible and expandable inner socket with a cavity with a volume and shape for receiving a substantial portion of the residual limb and fitting in said outer space between said socket and the residual limb, said inner socket having an inner surface and an outer surface, said inner surface adapted to oppose the residual limb, said outer surface opposing said outer socket;
  (c) a semi-compressible molding material disposed in said space;
  (d) a vacuum source;
  (e) a first vacuum valve connected to said vacuum source and said space;
  (f) a regulator means for controlling said vacuum source;
  (g) a power source connected to said regulator means and said vacuum source; and
  (h) a seal means for making an airtight seal between the residual limb and said outer socket
whereby said molding material conforms to the shape of the residual limb under the influence of said vacuum source.

27. The hypobarically-controlled artificial limb of claim 26, further comprising a second vacuum valve connected to said vacuum source and a vacuum tube connecting said vacuum valve to said cavity, thereby drawing the residual limb into firm contact with said inner surface of said inner socket.

28. The hypobarically-controlled artificial limb of claim 26, further comprising a positive air pressure source and a positive pressure valve connecting said space to said positive air pressure source, for compressing said inner socket as the volume of the residual limb decreases, said positive air pressure source being connected to said power source.

29. The hypobarically-controlled artificial limb of claim 26, further comprising a thin sheath to be disposed between the residual limb and said inner surface of said inner socket.

30. The hypobarically-controlled artificial limb of claim 29, further comprising a nonfoamed, nonporous polyurethane liner for receiving the residual limb and to be disposed between said sheath and the residual limb.

31. The hypobarically-controlled artificial limb of claim 29, wherein said sheath is thin knitted nylon.

32. The hypobarically-controlled artificial limb of claim 26, wherein said vacuum source is a motor-driven pump.

33. The hypobarically-controlled artificial limb of claim 26, wherein said positive pressure source is a motor-driven pump.

34. The hypobarically-controlled artificial limb of claim 26, wherein a motor-driven pump comprises both said vacuum source and said positive pressure source.

35. The hypobarically-controlled artificial limb of claim 26, wherein said regulator means is a digital computer.

36. The hypobarically-controlled artificial limb of claim 26, wherein said seal means comprises a nonfoamed, nonporous polyurethane suspension sleeve for rolling over and covering said socket and a portion of the residual limb, thereby forming an airtight seal.

37. The hypobarically-controlled artificial limb of claim 36, further comprising a stretchable nylon second sleeve for rolling over and covering said suspension sleeve to prevent clothing from sticking to and catching said suspension sleeve.

38. The hypobarically-controlled artificial limb of claim 26, wherein said semi-compressible molding material comprises polystyrene beads.

* * * * *